United States Patent [19]

Clark et al.

[11] Patent Number: 5,187,151

[45] Date of Patent: Feb. 16, 1993

[54] USE OF BINDING PROTEIN WITH IGF-I AS AN ANABOLIC GROWTH PROMOTING AGENT

[75] Inventors: Ross G. Clark, Pacifica; Venkat R. Mukku, Fremont, both of Calif.

[73] Assignee: Genentech, Inc., South San Francisco, Calif.

[21] Appl. No.: 654,436

[22] Filed: Feb. 12, 1991

[51] Int. Cl.$^5$ .................... A61K 37/26; C07K 5/00
[52] U.S. Cl. ........................... 514/3; 514/12; 514/21; 530/303; 530/324
[58] Field of Search ............ 514/3, 12, 21; 530/303, 530/324

[56] References Cited

U.S. PATENT DOCUMENTS 5,077,276 12/1991 Ballard et al. .

FOREIGN PATENT DOCUMENTS

| | | |
|---|---|---|
| 0294021 | 12/1988 | European Pat. Off. . |
| 0369943 | 5/1990 | European Pat. Off. . |
| 0375438 | 6/1990 | European Pat. Off. . |
| WO89/08667 | 9/1989 | PCT Int'l Appl. . |
| WO89/09268 | 10/1989 | PCT Int'l Appl. . |
| WO89/09792 | 10/1989 | PCT Int'l Appl. . |
| WO90/00569 | 1/1990 | PCT Int'l Appl. . |
| WO90/06950 | 6/1990 | PCT Int'l Appl. . |
| 8909792 | 10/1989 | World Int. Prop. O. . |
| 9000529 | 1/1990 | World Int. Prop. O. . |

OTHER PUBLICATIONS

Baxter & Martin, Progr. in Growth Factor Res., 1:49-68 (1989).
Nilsson et al., Science, 233: 571-574 (1986).
Elgin et al., PNAS USA, 84: 3254-3258 (1987).
Wood et al., Mol. Endocr., 2(12): 1176-1185 (1988).
Baxter & Martin, PNAS USA, 86: 6898-6902 (1989).
Lee et al., Mol. Endocr., 2(5): 404-411 (1988).
Walton et al., P.S.E.B.M., 190: 315-319 (1989).
Mevli et al., Diabetsologia, 14: 255-259 (1978).
Nilsson et al., J. Endocr., 122: 69-77 (1989).
Isaksson et al., Endocr. Revs., 8(4): 426-438 (1987).
Knaver & Smith, PNAS USA, 77(12): 7252-7256 (1980).
DeMellow & Baxter, BBRC, 156(1): 199-204 (1988).
Shimonaka et al., BBRC, 165(1): 189-195 (1989).
Mohan et al., PNAS USA, 86: 8338-8342 (1989).
Rosenfeld et al., J. Clin. Endocr. & Metab., 70(2): 551-553 (1990).
Binkert et al., EMBOJ., 8(9): 2497-2502 (1989).
Koistinen et al., Endocr., 118(4): 1375-1378 (1986).
Ballard et al., Acta Endocronologica, 121: 751-752 (1989).
Boghani et al., FEBS Lett., 255(2): 253-258 (1989).
Conover, Endocr. Soc. 72nd Ann. Mtg., Atlanta, Ga., Jun. 20-23, 1990, Abstr. 186.
Spencer et al., 2nd Intnl. Symp. on Insulin-Like Growth Factors/Somatomedins, San Francisco, Calif., Jan. 12-16, 1991, p. 269, Abstr. D-1.
Zapf et al., Growth Factors: From Genes to Clinical Application, Sara et al., Eds., Raven Press, NY (1990) pp. 227-251.
Blum et al., Endocr., 125(2): 766-772 (1989).
Baxter, Comp. Biochem. Physiol., 91B(2): 229-235 (1988).
Perkel et al., J. Clin. Endocr. & Metab., 71(2): 533-535 (1990).

(List continue on next page.)

*Primary Examiner*—Merrell C. Cashion, Jr.
*Assistant Examiner*—B. Celsa
*Attorney, Agent, or Firm*—Janet E. Hasak

[57] ABSTRACT

A method is disclosed for producing an anabolic state in a mammal by co-administration by subcutaneous injection of a combination of effective amounts of IGF-I and an IGF binding protein in a defined molar ratio in the absence of growth hormone so as to produce a greater anabolic response in the mammal than that achieved using IGF-I alone in an amount equal to that used for IGF-I in the combination. Preferably, the IGF-I is native-sequence, mature human IGF-I, the binding protein is IGFBP-3, and the mammal is human or a nonhuman animal of economic importance such as a cow or pig.

17 Claims, 10 Drawing Sheets

OTHER PUBLICATIONS

Talkington Verser et al., Proceed. Intern. Symp. Control. Rel. Bioact. Mater., 16: 223–224 (1989).
Bioventure View, vol. IV(1): 19–24 (Jan. 31, 1989).
Bantiota et al., Clin. Res., 38(1): 117A (1990).
Scheiwiller et al., Nature, 323: 169–171 (1986).
Binkert et al., EMBOJ., 8(9): 2497–2502 (1989).
Baxter, in Modern Concepts of Insulin-Like Growth Factors, Spencer, Ed., Elsevier Science Publishing Co., 1991 (pp. 371–380).
Drop et al., in Modern Concepts of Insulin-Like Growth Factors, Specner, Ed., Elsevier Science Publishing Co., 1991 (pp. 311'328).
Coleman & Etherton, J. Endocrinol., 128: 175–180 (1991).
Blum & Ranke, in Modern Concepts of Insulin-Like Growth Factors, Spencer, Ed., Elsevier Science Publishing Co., 1991 (pp. 381–393).
Clemmons et al., in Modern Concepts of Insulin-Like Growth Factors, Spencer Ed., Elsevier Science Publishing Co., 1991 (475–486).
Ross et al., Biochem. J., 258: 267–272 (1989).
Booth et al., Endocrinology, 127(6): 2630–2638 (1990).
Han et al., J. Neuroscience, 8(9): 3135–3143 (1988).
Liu et al., 2nd Internat'l Symposium on Insulin-Like Growth Factors/Somatomedins, Jan. 12–16, 1991, San Francisco, Calif. Abstract C37.
Clemmons et al., J. Biol. Chem., 265(21): 12210–12216 (1990).
Bioventure View vol. IV #1 (1989) 19–24.
Spencer, 2nd Inter IGF Sympos. Abstract.
Baxter & Martin Progress in Growth Factors Research vol. 1 pp. 49–68 (1989).
Rudinucr, Peptide Hormones (Parsons ed. 1976) 1–7.
Blum et al., Endo vol. 125 No. 2 (1989).

USE OF BINDING PROTEIN WITH IGF-I AS AN ANABOLIC GROWTH PROMOTING AGENT

BACKGROUND OF THE INVENTION

1. Field of the Invention

This invention relates to a method for producing an anabolic or growth promoting state in a mammal. More specifically, this invention is directed to the use of a complex of IGF-I and one or more of its binding proteins to produce an anabolic state, including enhancing whole body and bone growth.

2. Description of Related Disclosures

In the circulation, in other body fluids, and in media conditioned by cultured cells, the somatomedins (IGF-I and IGF-II) are bound to specific high-affinity carrier proteins that have been implicated as modulators of IGF actions. The history of IGF binding proteins (BPs) dates back to 1984 when the existence of specific somatomedin carrier proteins in serum was first shown. Hintz, *Clin. Endocrinol. Metab.*, 13: 31-42 (1984). Four distinct IGF BPs have now been cloned and sequenced, and in addition, several other, not yet thoroughly characterized, BP species have been identified in various tissues. See, e.g., Baxter and Martin, *Prog. in Growth Factor Res.*, 1: 49-68 (1989); Roghani et al., *FEBS Lett*, 255: 253-258 (1989); Bautista et al., *Clinical Res.*, 38: PA117 (1990). On the basis of the sequences it became evident that many of the previously recognized BPs, known by different names, were in fact the same, falling into a defined number of classes of cloned BPs. To clarify the present status of these BPs, the Workshop on IGF Binding Proteins, held in Vancouver, Canada, June 1989, proposed the names IGFBP-1, IGFBP-2, and IGFBP-3 for the binding proteins with defined sequences. Ballard et al., *Acta Endocrinol. (Copenh)*, 121: 751-752 (1989). The consensus at the Workshop was that other, incompletely characterized IGFBPs be referred to by size and origin until sequenced. Since that time, another IGFBP, namely, IGFBP-4, has been sequenced, as described below.

Amniotic fluid was the first source from which IGFBP-1 was detected Chochinov et al., *J. Clin. Endocrinol Metab.*, 44: 902-908 (1977). The protein has been purified also from tissue extract of fetal and maternal placenta and named placental protein. Kiostinen et al., *Endocrinology*, 118: 1375-1378 (1986). The mature protein contains 234 amino acids, predicting a molecular mass of 25.3 kD. Lee et al., *Mol. Endocrinol.*, 2: 404-411 (1988); WO 89/09792 published 19 October 1989. IGFBP-1 migrates on SDS-PAGE at 28-35 kD depending on the stage of reduction. IGFBP-1 is a minor binding protein in serum and contains the unsaturated serum IGF-binding sites. Serum levels are inversely dependent on insulin and have a marked diurnal variation, the levels being highest early in the morning. These levels increase in pregnancy up to several hundred µg/l, and amniotic fluid levels are up to 1000-fold higher than those in serum.

Carrier proteins of the IGFBP-2 class have been isolated from human fetal liver and rat and bovine cell lines. Binkert et al., *EMBO J.*, 8: 2497-2502 (1989); Rosenfeld et al., *J. Clin. Endocrinol. Metab.*, 70: 551-553 (1990). In humans, the mature form contains 289 amino acids and has an apparent molecular mass of 31-40 kD, depending on the stage of reduction on SDS-PAGE. In humans high IGFBP-2 levels have been found in the cerebrospinal fluid. The abundance of this protein in fetal tissue suggests that it has a role in regulating development. IGFBP-2 preferentially binds IGF-II.

The majority of serum IGFs are bound to a BP composed of two parts forming a complex of molecular mass 125-150 kD. IGFBP-3 is the IGF binding subunit ($\beta$-subunit) in this complex. Baxter and Martin, *Proc. Natl. Acad. Sci. USA*, 86: 6898-6902 (1989). It is an acid-stable glycoprotein appearing on SDS-PAGE as a major and minor band, corresponding to 53 and 47 kD, respectively. The other components in the complex are the acid-labile, non-IGF-binding subunit ($\alpha$-subunit) with a molecular mass of 84-86 kD [Baxter, WO 90/0569], and IGF-I or IGF-II ($\gamma$-subunit). Sequencing of the cloned cDNA for IGFBP-3 (previously known as IGFBP-53) predicts a molecular mass of 28.7 kD for the non-glycosylated protein and reveals that IGFBP-3 shares 33% sequence identity with IGFBP-1. Wood et al., *Mol. Endocrinol.*, 2: 1176-1185 (1988); WO 89/09268 published Oct. 5, 1989.

Most recently, a 25-kD IGFBP-4 has been isolated from cultured human osteoblast-like TE89 osteosarcoma cell conditioned media and sequenced. Mohan et al., *Proc. Natl. Acad. Sci. USA*, 86: 8338-8342 (1989). A similar, if not identical, IGFBP was isolated from human prostatic carcinoma cells and sequenced. Perkel et al., *J. Clin. Endocrin. and Metab.*, 71: 533-535 (1990)]. Another similar IGFBP was identified in adult rat serum. Shimonaka et al., *Biochem. Biophys. Res. Comm.*, 165: 189-195 (1989).

The levels of IGFBP in adult serum have been found to reflect the growth hormone (GH) status of individuals who are either GH-deficient or acromegalic. Thus, high levels of IGFBP-3 correlate with high levels of GH. Martin and Baxter, *J. Clin. Endo. and Metabol.*, 61: 799-801 (1985). Under normal conditions about 95-98% of the IGF-I in human plasma is bound to the IGFBPs. Studies on size-fractionated human serum, subjected to IGF-I RIA after extraction of each fraction to remove binding activity, have indicated that 72% of the endogenous peptide is associated with the 150-kD fraction and 25% with the 50-kD fraction. Daughaday et al., *J. Clin. Endocrinol. Metab.*, 55: 916-921 (1982).

The literature has ascribed to IGFBP-3 both a passive role as a carrier of IGF-I extending its circulatory half-life and an active role as a promoter of IGF-I activity. For example, it has been disclosed by BioGrowth, Inc. that IGFBP-3 significantly accelerates healing in an animal wound-healing model and that the complex of IGF-I and IGFBP-3 stimulates cortical and trabecular bone growth in rats in preliminary experiments, suggesting that the BP may be useful in treating osteoporosis. See *Bioventure View*, Vol. IV, No. 1 (Jan. 31, 1989), pages 19-20. See also EP 294,021 and 375,438 to BioGrowth, Inc. disclosing use of IGFBP-3 in conjunction with IGF-I or -II to treat diseases such as osteoporosis and human GH deficiency, and to heal wounds and increase animal growth, including delivery to bony tissues to stimulate bone growth (see, e.g., p. 8 of EP 294,021 and p. 11 of EP 375,438). See also WO 90/00569 published Jan. 2, 1990. No data are provided for these speculative uses. There is one suggestion by BioGrowth scientists that IGFBP-3 (called IGF-CP) apparently increases IGF-directed bone growth in rats. Talkington-Verser et al., *Proceed. Intern. Symp. Control. Rel. Bioact. Mater.*, 16: 223-224 (1989). However, no protocols or data are provided.

It has also been disclosed that a 28-kD IGFBP from human placental and hepatoma cDNA libraries administered together with IGF-I, IGF-II, or other growth factors or formulated as common preparations for topical use in therapeutic devices useful for healing wounds or bones or for treating osteoporosis might be valuable for a steady, controlled release of the somatomedins in such devices. WO 89/08667, published Sep. 21, 1989, pages 8-9.

Another human BP equivalent to that of rat BRL-3A is reported in EP 369,943 published May 23, 1990 to be useful in combination with an IGF to treat, e.g., osteoporosis, Laron-type dwarfism, anemias, hypopituitarism, and wounds (see col. 15). IGF-I and -II BPs having IGF potentiating and inhibiting activities are described in WO 89/09792 published Oct. 19, 1989.

Further, based on studies using baby hamster kidney and human skin fibroblasts, it has been suggested that IGFBP acts as a reservoir, releasing continuously low amounts of IGF-I and thus creating a steady-state situation of receptor occupancy, which appears to be a better mitogenic stimulus than temporary large concentrations of IGF-I. Blum et al., *Endocrinology*, 125: 766-772 (1989).

However, several recent reviews cast further doubt on the precise biological activities of the IGFBPs. For example, Zapf et al., *Growth Factors: From Genes to Clinical Application*, Karolinska Nobel Conference Series, Eds. Vicki Sara et al., (Raven Press 1990), p. 227] states that inhibitory as well as enhancing effects of IGF carrier proteins on IGF actions have been observed in vitro, citing DeMellow et al., *Biochem. Biophys. Res. Comm.*, 156: 199-204 (1988); Elgin et al., *Proc. Natl. Acad. Sci. USA*, 84: 3254-3258 (1987); Knauer and Smith, *Proc. Natl. Acad. Sci. USA*, 77: 7252-7256 (1980); Meuli et al., *Diabetologia*, 14: 255-259 (1978); Schweiwiller et al., *Nature*, 323: 169-171 (1986). Zapf et al. further state that it is still unknown whether the different IGFBP species known thus far differ with respect to inhibiting or enhancing the growth promoting effects of IGF.

On page 241 of the same book, Hall et al. state that, in general, IGFBP-1, similar to IGFBP-3, is found to inhibit IGF-I stimulation of amino acid uptake and DNA synthesis, citing, inter alia, Walton et al., *P.S.E.B.M.*, 190: 315-319 (1989).

A 1988 review article reports that despite increasing interest in IGFBPs in recent years, their functions are still poorly understood. Baxter, *Comp. Biochem. Physiol.*, 91B, 229-235 (1988), p. 232-233. Baxter points to some evidence that association with BPs may not always inhibit the activity of the IGFs and that cell types producing the BPs might be able to enhance their IGF responsiveness in an autocrine fashion. Examples cited are that some high molecular weight complexes from human plasma retain biological activity in rat adipocyte assays for insulin-like activity, cultured human fibroblasts secrete a BP of 35 kD that increases cell IGF binding, and a pure preparation of amniotic fluid BP significantly potentiates the effect of IGF-I in stimulating DNA synthesis in porcine smooth muscle cells and fibroblasts from various species. Furthermore, it has been shown that IGFBP-3 blocks the hypoglycemic action of IGF-I when administered subcutaneously together with the IGF-I in a 1:1 ratio. Spencer et al., 2nd International Symposium on Insulin-Like Growth Factors/Somatomedins, January 12-16, 1991, program and Abstracts p. 269.

Another view is that IGFBPs are produced locally in all tissues to concentrate locally produced IGF-I near cells requiring the IGF-I, reducing the active role of IGF-I bound to BPs and IGF-I circulating in the blood. Isaksson et al., *Endocrine Reviews*, 8: 426-438 (1987). It has been reported, for example, that IGF-I is produced locally in bone by GH [Nilsson et al., *Science*, 233: 571-574 (1986)], and GH receptors have been found on chondrocytes. Nilsson et al., *J. Endocr.*, 122: 69-77 (1989).

Furthermore, the recent work of Conover, 72nd Annual Meeting of Endocrine Society, Prog. Abstract 186 (June 1990) shows in vitro that the activity of the IGFBPs, in enhancing the activity of IGF-I, is dependent on cells being exposed to the BPs alone. There was no response to IGF-I in cells incubated with pre-mixed BP and IGF-I. If the BP was incubated with the cells by itself, followed by addition of IGF-I, the activity of the added IGF-I was enhanced. These data suggest that co-mixing IGF and a IGFBP and co-injecting the complex would not result in an enhancement of the activity of the IGF-I.

It is an object of the present invention to provide a specific method for promoting the growth of mammals by administering through subcutaneous injection a complex of IGF-I and a IGFBP.

It is another object to provide a way to administer large doses of IGF-I to a patient without concern for hypoglycemia.

These and other objects will be apparent to one of ordinary skill in the art.

SUMMARY OF THE INVENTION

Accordingly, this invention provides a method for producing an anabolic state in a mammal comprising co-administering to the mammal by subcutaneous bolus injection effective amounts of IGFBP and IGF-I in a molar ratio of IGFBP to IGF-I of about 0.5:1 to about 3:1 so as to produce a greater anabolic state in the mammal than that achieved using an equivalent dose of IGF-I alone, wherein growth hormone is not also administered to the mammal.

Preferably, the IGFBP is IGFBP-3. Co-administration of IGF-I and IGFBP-3 gave a greater growth response than three-fold more IGF-I alone. Without limitation to any one theory, it is believed that this effect may be a pharmacokinetic or half-life phenomenon or that the IGFBP allows IGF-I to have an anabolic effect despite being bound. IGFBP blocks hypoglycemia but not the anabolic effect of IGF-I, so that large doses of IGF-I can be given without the risk of acute hypoglycemia. Subcutaneous injections of IGF-I coupled to a IGFBP are found to be effective for growing bones, increasing cartilage plate width, and having an overall anabolic effect. In contrast, IGF-I by itself is relatively inactive when given by subcutaneous injections. The fact that the data show a general anabolic effect in the whole mammal, including whole body weight gain and an increase in organ weight, implies that an anabolic effect would be observed in other situations, e.g., in states of nutritional stress.

BRIEF DESCRIPTION OF THE DRAWINGS

FIG. 8 illustrates bar graphs of the growth rate in cm/year of patients of various growth inhibition etiologies having had either no previous treatment (Prev Rx No) or previous treatment (Prev Rx Yes) with hGH. N indicates the number of patients at the indicated dose level of hGH given in units of mg/kg.

DESCRIPTION OF THE PREFERRED EMBODIMENTS

Definitions

Figure 1:
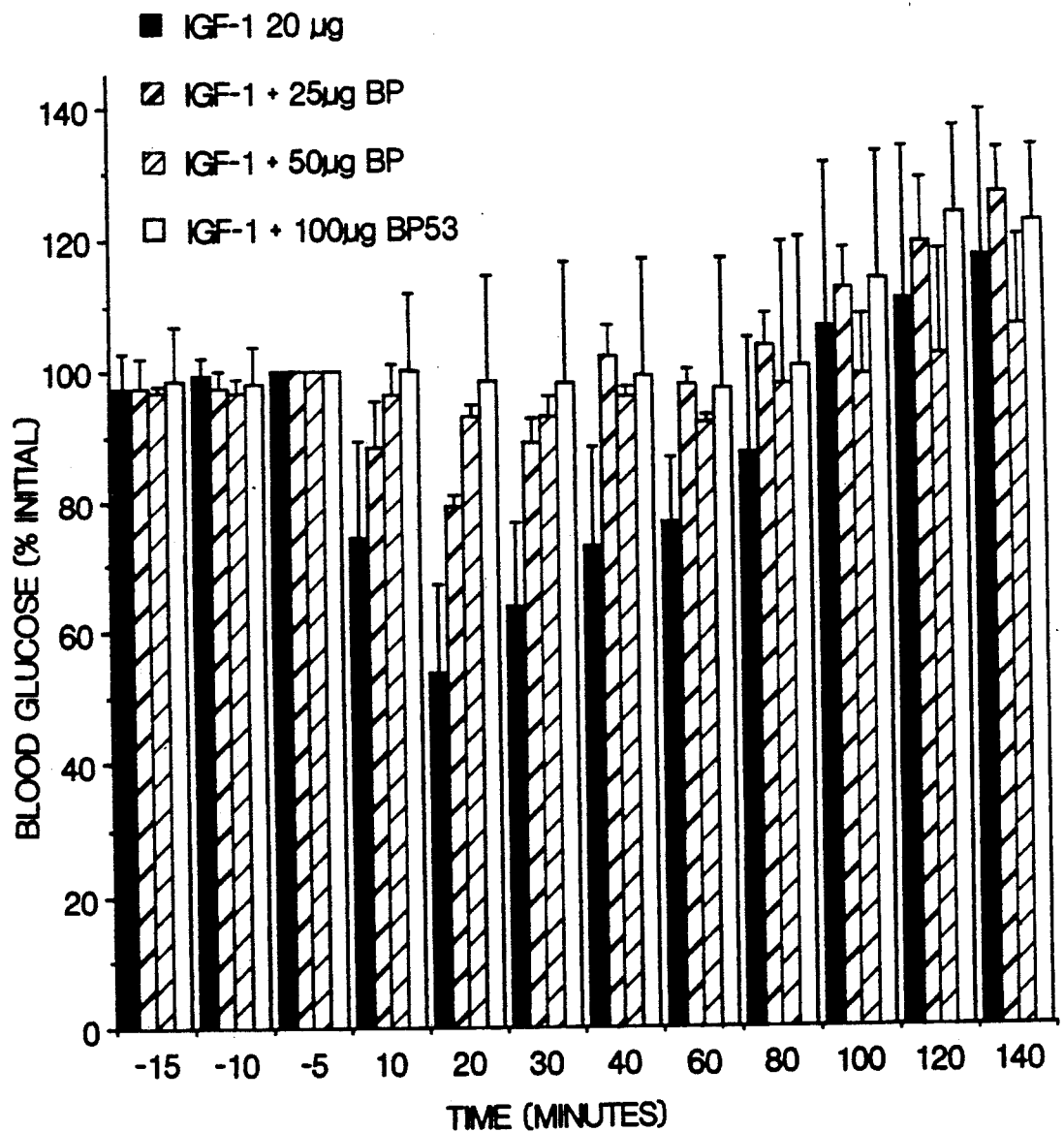
FIG. 1 illustrates 20-minute blood glucose values normalized to initial blood glucoses, for IGF-I alone and IGF-I plus IGFBP-3 injected i.v. to rats for one experiment.

As used herein, "IGF-I" refers to insulin-like growth factor-I from any species, including bovine, ovine, porcine, equine, and preferably human, in native-sequence or in variant form, and from any source, whether natural, synthetic, or recombinant, provided that it will bind to an IGFBP at the appropriate site. Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations. Also preferred for use is IGF-I that has a specific activity greater than about 14,000 units/mg as determined by radioreceptor assay using placenta membranes, such as that available from KabiGen AB, Stockholm, Sweden.

The most preferred IGF-I variants are those described in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1-3)-IGF-I, or des-IGF-I).

As used herein, "IGFBP" refers to a protein that binds IGF-I in the circulation, in other body fluids, and in media conditioned by cultured cells, as defined in the Workshop on IGF Binding Proteins held in Vancouver, Canada in June 1989 discussed above and reported in Ballard et al., *Acta Endocrinol.* (Copenh), 121: 751-752 (1989). This term includes IGFBP-1, IGFBP-2, IGFBP-3, IGFBP-4, IGFBP-5, IGFBP-6, and other as yet unidentified IGFBPs that have the characteristics common to all the known IGF binding proteins. The term includes animal equivalents to human IGFBPs as well as human IGFBPs, for example, the bovine, ovine, porcine, and equine species. It may be from any source, whether natural, synthetic, or recombinant, provided that it will bind to the appropriate binding domain of IGF-I.

As used herein, "ALS" refers to the acid-labile, 84-86 kD, non-IGF-binding subunit of the 125-150 kD complex With IGFBP-3 and IGF-I as described in Baxter, WO 90/0569 or any animal equivalent thereof, preferably human ALS. It may be from any source, including natural, synthetic, or recombinant sources.

As used herein, "IGFBP-3" is defined as described above and in WO 89/09268 published Oct. 5, 1989 and Wood et al., *Molecular Endocrinology*, supra, but includes animal equivalents to human IGFBP-3 as well as human IGFBP-3, for example, the bovine, ovine, porcine, and equine species. It may be from any source, whether natural, synthetic, or recombinant, provided that it will bind to the appropriate binding domain of IGF-I.

As used herein, "mammal" signifies humans as well as animals. Mammals that are candidates for treatment include animals of economic importance such as bovine, ovine, and porcine animals. The preferred mammal herein is a human.

As used herein, the words "producing an anabolic state" refer to promoting total body weight gain as well as the dynamics of statural growth experienced by an individual during infancy, childhood, and adolescence as depicted by a normal growth curve, i.e., growth of linear-producing bone plate driven by chondrocytes, as well as growth of osteoblast cells, derived from a different part of the bone. Restoration of normal growth patterns would allow the patient to approach a more satisfactory growth curve. Examples of patients that are relatively resistant to GH but require treatment to induce an anabolic effect include those with Turner's Syndrome, GH-deficient children who grow poorly in response to GH treatment, children who experience a slowing or retardation in their normal growth curve about 2-3 years before their growth plate closes, so that GH administered alone would no longer increase growth of the children, so-called short normal children, and patients where the IGF-I response to GH has been blocked chemically (i.e., by glucocorticoid treatment) or by a natural condition such as in adult patients where the IGF-I response to GH is naturally reduced. In addition, the method herein is useful for treating pregnant women who are in a catabolic state and/or experience loss of bone mass, for treating women with osteoporosis, and for repairing bone.

Modes for Carrying Out the Invention

The method herein involves co-administering the IGF-I and IGFBP in a molar ratio of IGFBP to IGF-I of about 0.5:1 to 3:1 by subcutaneous (sc) bolus injection. The IGF-I and IGFBP mixture to be used in the therapy will be formulated and dosed in a fashion consistent with good medical practice, taking into account the clinical condition of the individual patient (including any perceived or anticipated side or reduced anabolic effects using IGF-I alone), the particular growth defect or catabolic state to be corrected, the particular IGFBP being utilized, the site of delivery of the mixture, and other factors known to practitioners.

The "effective amounts" of IGF-I and IGFBP for purposes herein are thus determined by such considerations, with the understanding that the two drugs will be premixed in a molar ratio of IGFBP to IGF-I in the range of about 0.5:1 to about 3:1 before administration, and with the understanding that the amounts administered will promote a greater anabolic state in the treated patient over the anabolic effect obtained using the same amount of IGF-I administered by the same protocol, regimen, and route, but without IGFBP being also administered.

The IGFBP may be one IGFBP or a mixture of two or more IGFBPs. The preferred IGFBP employed is IGFBP-3. IGFBP-3 is optionally also accompanied by ALS as a third component of the mixture, in a molar ratio of at least about 1:1 of ALS to IGFBP-3. The presence of the ALS will permit formation of the 125–150-kD three-component complex in which IGF-I is carried naturally in the blood.

The administration takes place in the absence of administration of GH, i.e., any species of growth hormone or growth hormone variant such as recombinant hGH, e.g., methionyl human growth hormone as described in U.S. Pat. No. 4,755,465 issued Jul. 5, 1988 and Goeddel et al., *Nature*, 282: 544 (1979), and rhGH available to clinical and research investigators from Genentech, Inc. under the trademark Nutropin®, and commercially available from Eli Lilly, that lacks the N-terminal methionine.

As a general proposition, the total pharmaceutically effective amount of the IGF-I administered sc per dose will be in the range of about 1 µg/kg/day to 100 mg/kg/day of patient body weight, although, as noted above, this will be subject to a great deal of therapeutic discretion, and due to possible hypoglycemic effects of using IGF-I alone, the maximum dose of IGF-I will be lower than if it were to be used alone. Preferably, this dose is at least 0.1 mg/kg/day, and more preferably about 1–20 mg/kg/day. Most preferably, the dose of IGF-I employed is one that will not by itself cause hypoglycemia in the patient, so that if degradation of the IGF-I/IGFBP complex or IGFBP takes place, the excess IGF-I that remains free will not be detrimental to the patient.

The total pharmaceutically effective amount of the IGFBP administered sc per dose will be generally be such that the molar ratio of IGFBP to IGF-I is about 0.5:1 to about 3:1, preferably about 0.8:1 to 1.5:1. If the molar ratio is less than about 0.5:1, the excess IGF-I that is not bound up by the IGFBP may have an undesired hypoglycemic effect, but if the ratio is greater than about 3:1, the activity of the IGF-I may be considerably reduced. The key factor in selecting an appropriate dose is the result obtained, which optimally minimizes the side effects, particularly hypoglycemia, while maximizing the efficacy. Efficacious results are measured by increases in body weight gain, lean body mass, bone growth, or statutory growth approximating the normal range, or by other criteria for measuring the anabolic state of a mammal, as defined herein, as are deemed appropriate by the practitioner.

While the mixture of IGF-I and IGFBP represents in itself a sustained-release formulation of IGF-I since the IGF-I is complexed to the BP, the IGF-I and IGFBP mixture is also suitably administered with another agent known to generate a sustained-release formulation compatible with sc bolus injection. Such compositions include liposomally entrapped IGF-I and IGFBP. Liposomes containing IGF-I and IGFBP are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal IGF-I/IGFBP therapy.

For sc administration, the IGF-I and IGFBP are formulated generally by mixing them together at the desired degree of purity, in a unit dosage injectable form (solution, suspension, or emulsion), and adding or mixing simultaneously a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. The mixture also preferably contains a stabilizer, such as a protease inhibitor, e.g., aprotinin, that will not allow the combined formulation of IGF-I and IGFBP to degrade in the storage container or after injection.

Generally, the formulations are prepared by contacting the IGF-I and IGFBP uniformly and intimately with liquid carriers. Preferably the carrier is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts, preferably citrate for full-length IGF-I; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA: sugar alcohols such as mannitol or sorbitol; counterions such as sodium; and/or nonionic surfactants such as polysorbates, poloxamers, or PEG.

The IGF-I and IGFBP are typically formulated for injection in such vehicles at a concentration of about 0.1 mg/ml to 100 mg/ml, preferably 1-10 mg/ml, at a pH of about 4.5 to 8. Full-length IGF-I is generally stable at a pH of no more than about 6. It will be understood that use of certain of the foregoing excipients, carriers, or stabilizers will improve the stability of the IGF-I/IGFBP complex.

IGF-I and IGFBP to be used for therapeutic administration must be sterile. Sterility is readily accomplished by filtration through sterile filtration membranes (e.g., 0.2 micron membranes). Therapeutic IGF-I and IGFBP compositions generally are placed for storage into a unit or multi-dose container having a sterile access port, for example, a sealed ampoule, bag, or vial having a stopper pierceable by a hypodermic injection needle. The composition will be stored as an aqueous solution or as a lyophilized formulation for reconstitution. As an example of a lyophilized formulation, 10-ml vials are filled with 5 ml of a sterile-filtered 1% (w/v) aqueous solution of IGF-I and IGFBP-3, and the resulting mixture is lyophilized. The injection solution is prepared by reconstituting the lyophilized IGF-I using bacteriostatic Water-for-Injection.

The following examples are intended to illustrate one embodiment now known for practicing the invention, but the invention is not to be considered limited to these examples. All academic and patent literature citations herein are expressly incorporated by reference.

EXAMPLE I

Effect of IGFBP on Blood Glucose Levels

Summary

In two separate studies IGF-I was injected by itself or combined and co-injected with various doses of IGFBP-3. Basal blood samples, then blood samples following the protein injections, were taken. Blood glucose was measured in the separated plasma. IGF-I by itself caused the expected fall in blood glucose. In a dose-related fashion the IGFBP-3 inhibited the ability of IGF-I to reduce blood glucose. In a repeat experiment this observation was confirmed using a dose of IGFBP-3 seen to be effective in the initial experiment. The IGFBP-3 was inactive by itself.

Design

In two separate experiments female dwarf rats (60 to 70 days of age, 100 to 140 g) were anaesthetized with ketamine/xylazine, and a jugular cannula was implanted for blood sampling. Blood sampling was performed using an automated blood sampling device so that 12 rats could be sampled simultaneously. Three (Exp. 1) or two (Exp. 2) basal blood samples, each of 100 microliters, were taken at five-minute intervals. The test substances were then administered by bolus injection via the jugular catheter. Blood samples were taken at 10-minute intervals for 40 minutes and then at 20-minute intervals until 120 minutes following the injections. The samples were centrifuged and the plasma was retained and analyzed for glucose using the Monarch 2000 blood chemistry analyzer.

Test Substances and Doses

Recombinant human IGF-I produced in *E. coli* by the process generally described in EP 230,869 published Aug. 5, 1987, or available commercially from KabiGen AB, Stockholm, Sweden (specific activity > 14,000 U/mg by radioreceptor assay using placental membranes), or available for clinical investigations from Genentech, Inc., South San Francisco was employed in citrate buffer at 5 mg/ml. The recombinant IGFBO-3 was expressed in mammalian cells and purified as described in WO 89/09268 published Oct. 5, 1989; Wood et alk. *Molecular Endocrinology*, supra; Mukku et al., *Insulin-like Growth Factor Binding Proteins*, Drop and Hintz, eds. (Elsevier Science Publishers, 1989).

Exp. 1

IGF-I was diluted to 50 μg/ml and 0.5 ml of this solution was given to the rats (25 μg/rat). Various concentrations of IGFBP-3 were incubated overnight with IGF-I (at 50 μg/ml). The IGFBP-3 concentrations were 50, 100, and 200 μg/ml, so that 25, 50, and 100 μg of IFGBP-3 were co-injected with 25 μg of IGF-I.
1) Three animals were given 25 μg of IGF-I.
2) Three animals were given 25 μg of IGF-I + 25 μg of IGFBP-3.
3) Three animals were given 25 μg of IGF-I + 50 μg of IGFBP-3.
4) Three animals were given 25 μg of IGF-I + 100 μg of IGFBP-3.

Exp. 2

IGF-I and IGFBP-3 were prepared and administered as described above. In this experiment only one dose of IGFBP-3 was combined with the IGF-I and the IGFBP-3 was administered by itself.
6) Four animals were given 25 μg of IGF-I.
7) Four animals were given 50 μg of IGFBP-3.
8) Four animals were given 25 μg of IGF-I and 50 μg of IGFBP-3.

Results

FIG. 1 shows the complete results from Exp. 1. The data have been normalized so that the −5 minute blood sample before the injection of the test substances is the 100% value. Blood glucose can be seen to be stable before the injections. IGF-I caused a fall in blood glucose to 53±13% (Mean±SD). With increasing doses of the IGFBP this response was blocked in a graded manner.

Figure 2:
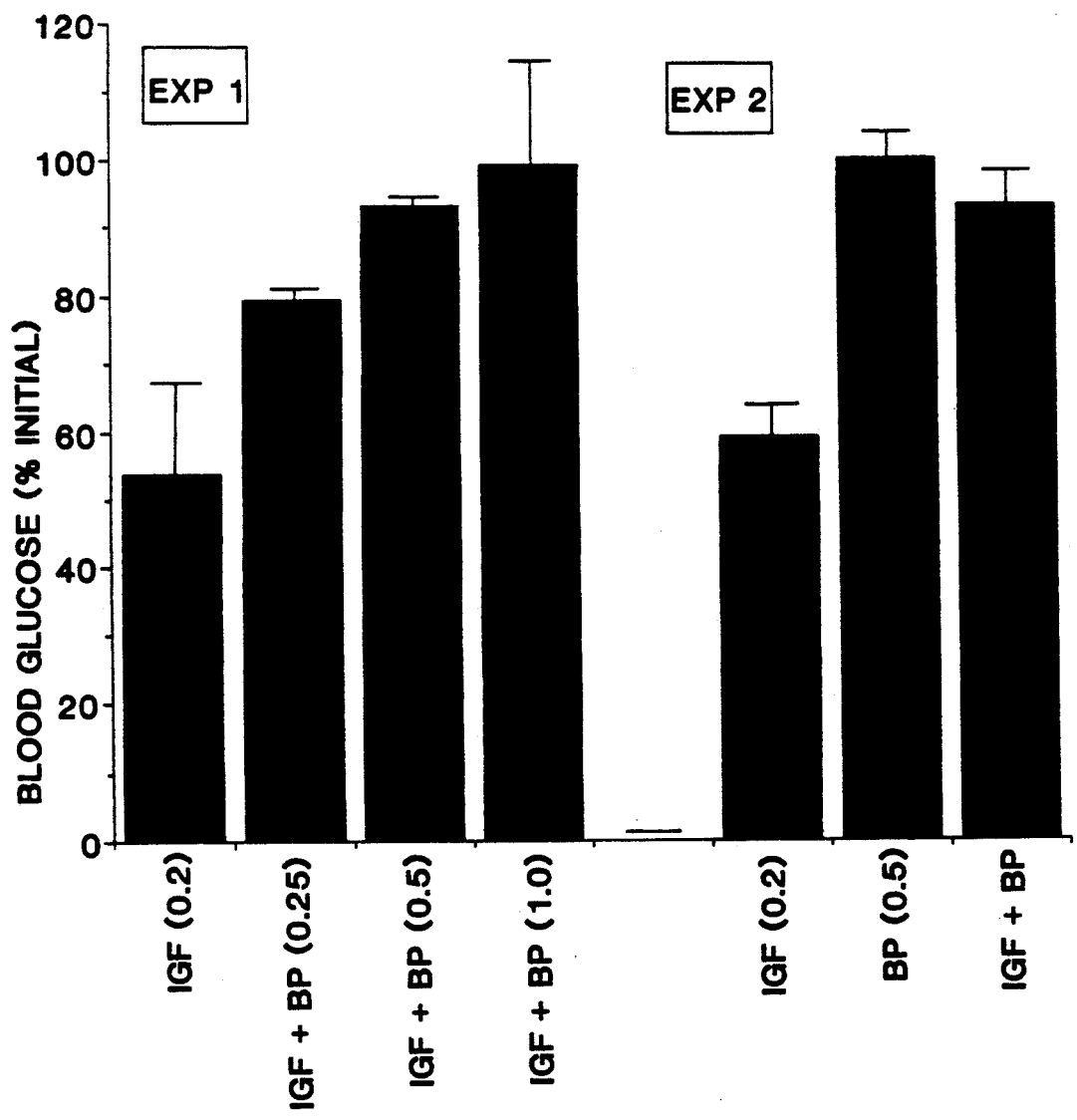
FIG. 2 illustrates the same data as FIG. 1 for a second experiment.

FIG. 2 shows the 20-minute blood glucose values, again normalized to initial blood glucose levels, for both experiments 1 and 2 (Groups 1 to 4, and 6 to 8 described above). In Exp. 2 IGF-I caused blood glucose to fall so that at 20 minutes it was 58±5% of the initial level. This level was no different from that induced in Exp. 1. In Exp. 2 the IGFBP-3 alone did not affect blood glucose (99±4% of initial) and at 20 minutes IGFBP-3+IGF-I caused blood glucose to be 93±5% of the initial level.

EXAMPLE II

Delivery by Continuous Infusion

Protocol

Twenty-two hypophysectomized rats (Taconic, Germantown, N.Y.) of 85-105 g were weighed four times over ten days to establish growth stasis (weight gain or loss of less than 7 grams). They ate pelleted lab diet and drank water ad libitum. They were group housed (5/cage) in a room controlled for lighting and temperature. They were then randomized into three groups of rats based on their initial body weight. The rats were anaesthetized with ketamine/xylazine, and two osmotic minipumps (2001, delivery rate 1 μl/hr/pump) were placed subcutaneously. The rats were weighed daily and after seven days they were sacrificed and various body organs were removed.

The IGF-I employed for this experiment was the IGF-I employed in Example I in citrate buffer at 5 mg/ml. The IGFBP-3 used was that described in Example I. The pumps contained either the excipient (citrate buffer), or IGF-I, or IGF-I plus IGFBP-3 so that the experimental groups were:
1) Excipient pumps (n=8)
2) IGF-I delivery at 0.3 mg/kg/day (n=8)
3) IGF-I delivery at 0.3 mg/kg/day plus IGFBP-3 delivery at 0.9 mg/kg/day (n=6).

Results

Figure 3:
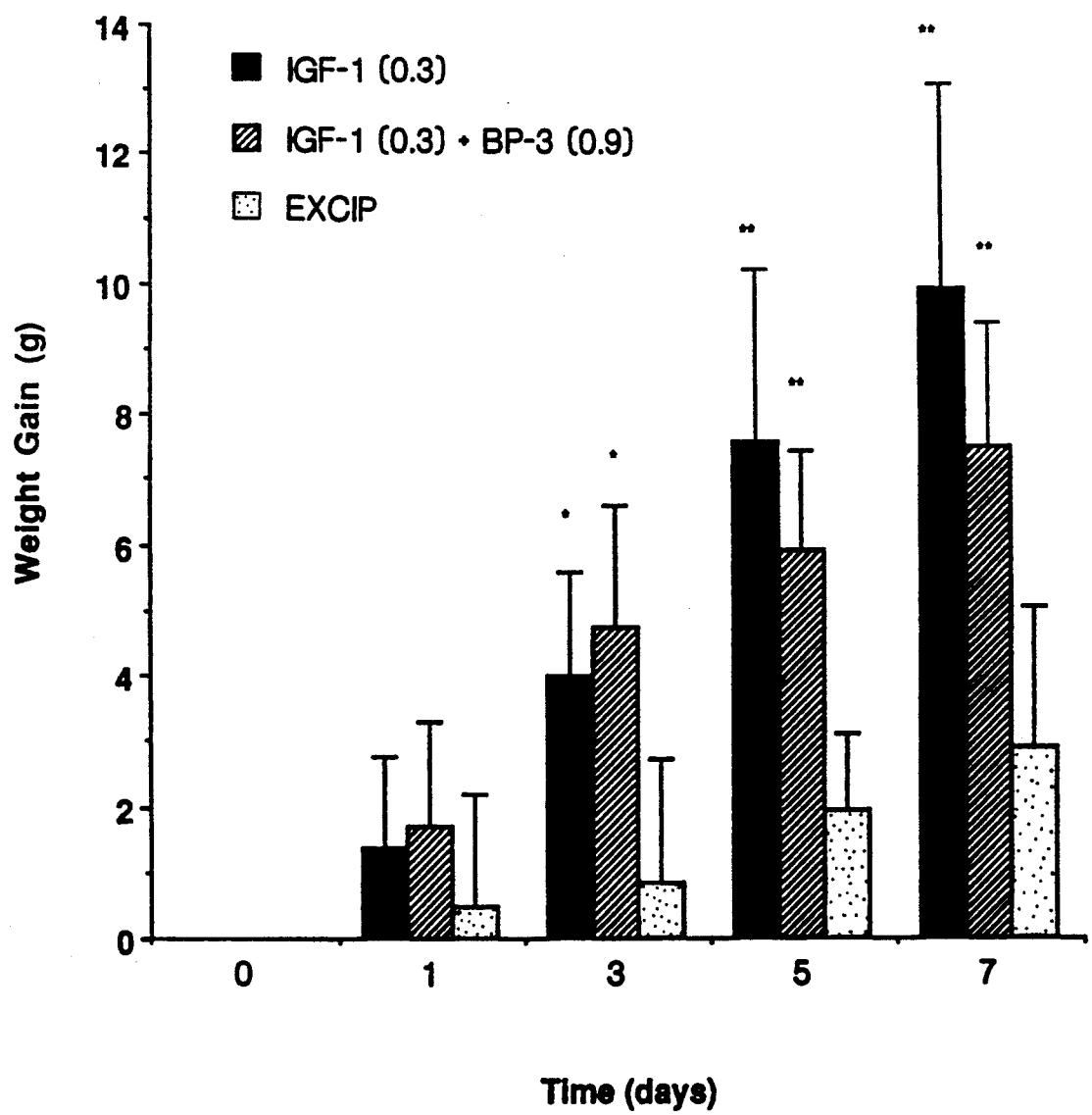
FIG. 3 illustrates a graph showing the effect of excipient, IGF-I, and IGF-I plus IGFBP-3 on weight gain in hypophysectomized rats to which the reagents are administered via minipumps for seven days, with doses indicated in mg/kg/day.

FIG. 3 shows the weight gains over seven days. Excipient-treated hypophysectomized rats showed the expected lack of weight gain during the experimental period. The dose of IGF-I used (0.3 mg/kg/day) produced the weight gain expected for this dose when given by s.c. infusion. When IGF-I was delivered coupled to IGFBP-3 in a 1:1 molar ratio, the IGF-I-induced weight gain was not significantly reduced.

Figure 4:
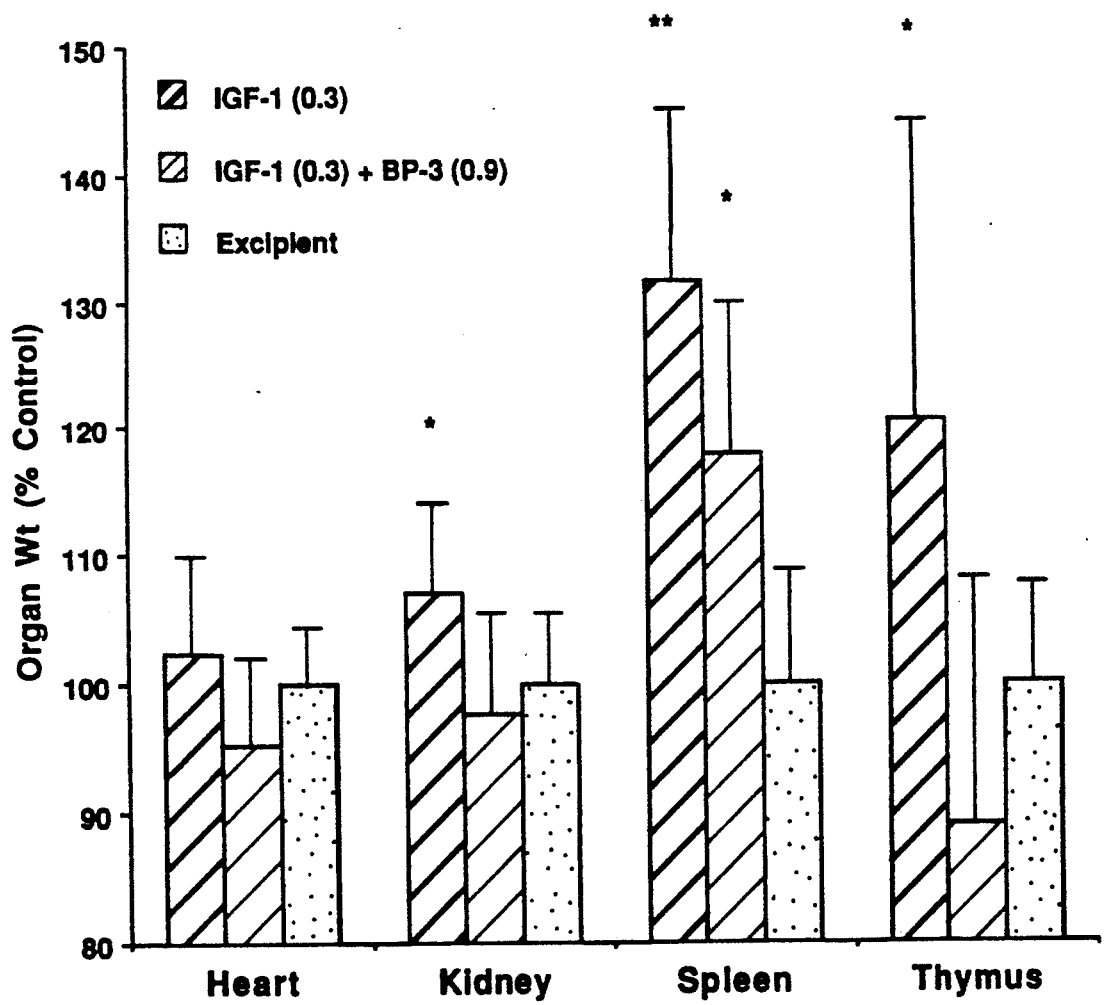
FIG. 4 illustrates a graph showing the effect of excipient, IGF-I, and IGF-I plus IGFBP-3 on various organ weights of the hypophysectomized rats treated as described for FIG. 3, with organ weight expressed as a percent of excipient-treated controls.

FIG. 4 shows the effect of IGFBP-3 on organ weight response to the IGF-I-treated rats. The thymus, spleen, and kidney all showed the expected significantly increased wet weights following IGF-I treatment. However, these IGF-I-sensitive organs reacted differently to the presence of the IGFBP-3. There was a significant growth response of the spleen when IGF-I and IGFBP-3 were co-delivered; however, the thymus and the kidney did not show significant growth responses.

In both FIGS. 3 and 4, statistical comparisons were made by an analysis of variance (ANOVA) with follow-up comparisons made by Duncan's Multiple Range Test. A p value of less than 0.05 was considered significant. All data are represented as the mean ±SD of 6-8 animals per group. The asterisks indicate statistical significance compared to excipient-treated controls (* $p<0.05$, ** $p<0.01$).

EXAMPLE III

Delivery by sc Injection

Figure 5:
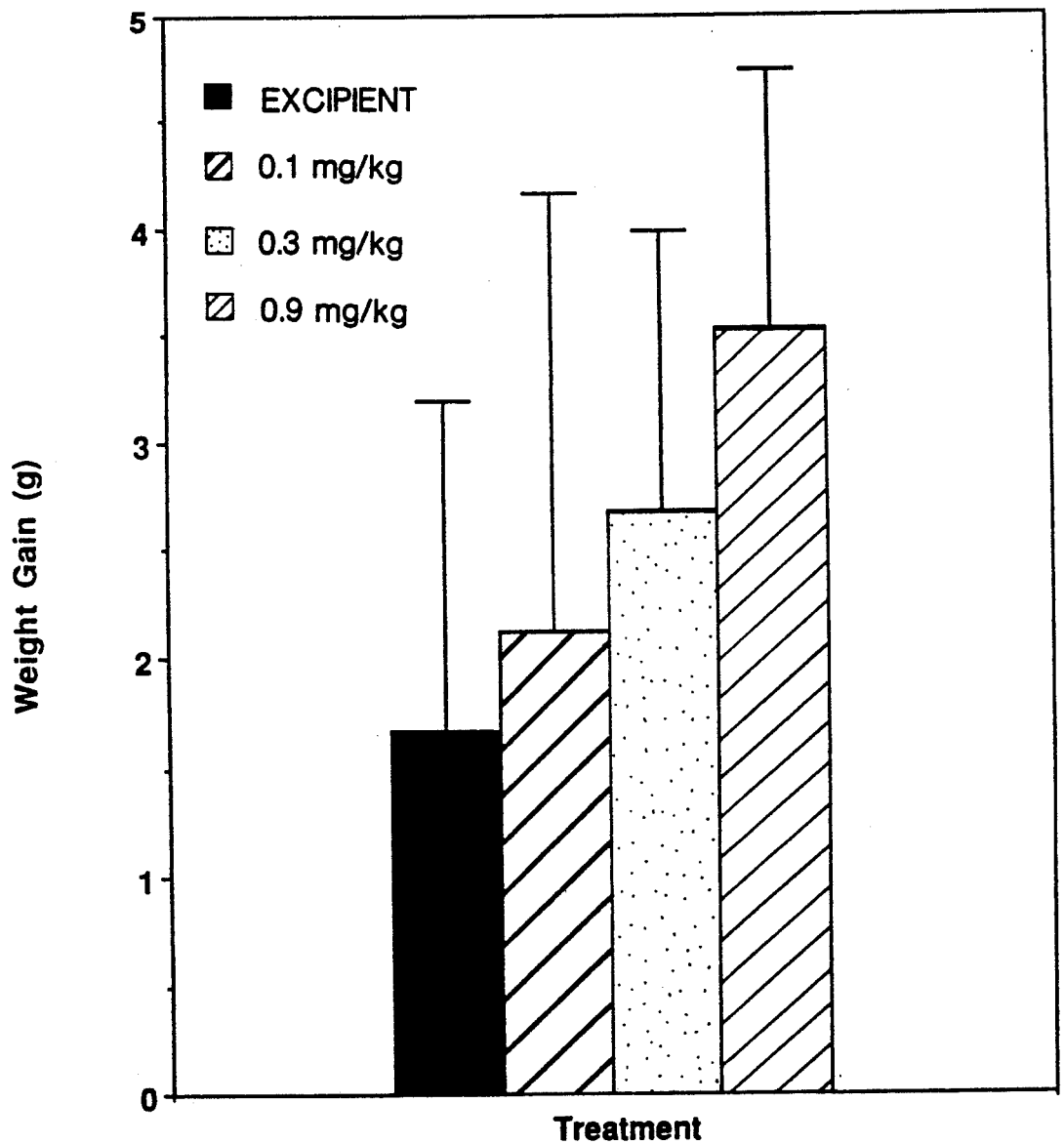
FIG. 5 illustrates a graph showing the effect on weight gain of IGF-I delivered in three different doses by sc injection twice daily in the indicated amounts for three days to hypophysectomized rats.

In a preliminary experiment it was determined that IGF-I (as described in Examples I and II) given subcutaneously as twice daily injections for three days (six injections) had a very small effect on weight gain in the hypophysectomized rat compared to the much larger effect of sc infusions of IGF-I by minipump. FIG. 5 shows the weight gain for sc injections of three different doses of IGF-I.

In a new experiment to test the effect of IGFBP-3 on sc injections of IGF-I, 26 female hypophysectomized rats (Taconic, Germantown, N.Y.) of 85-105 g were weighed four times over ten days to establish growth stasis as defined above. They ate pelleted lab diet and drank water ad libitum. They were group housed (5/cage) in a room controlled for lighting and temperature. They were then randomized into three groups of rats based on their initial body weight. The rats were given twice daily sc injections of 0.1 ml each at 8 am and 5 pm on days 0, 1, and 2 (6 injections in all). Body weight measurements were made at the morning injections. The rats were sacrificed on day 3 (approximately 16 hours following the sixth injection) and various body organs were removed. The IGF-I and IGFBP-3 were those used in Examples I and II. The experimental groups were:
1) Excipient injections
2) IGF-I delivery at 0.3 mg/kg/day (two injections of 15 µg per day)
3) IGF-I delivery at 0.9 mg/kg/day (two injections of 45 µg per day)
4) IGF-I delivery at 0.3 mg/kg/day plus IGFBP-3 delivery at 0.8 mg/kg/day (two injections of 15 µg of IGF-I plus 40 µg of IGFBP-3 per day).

Results

Figure 6:
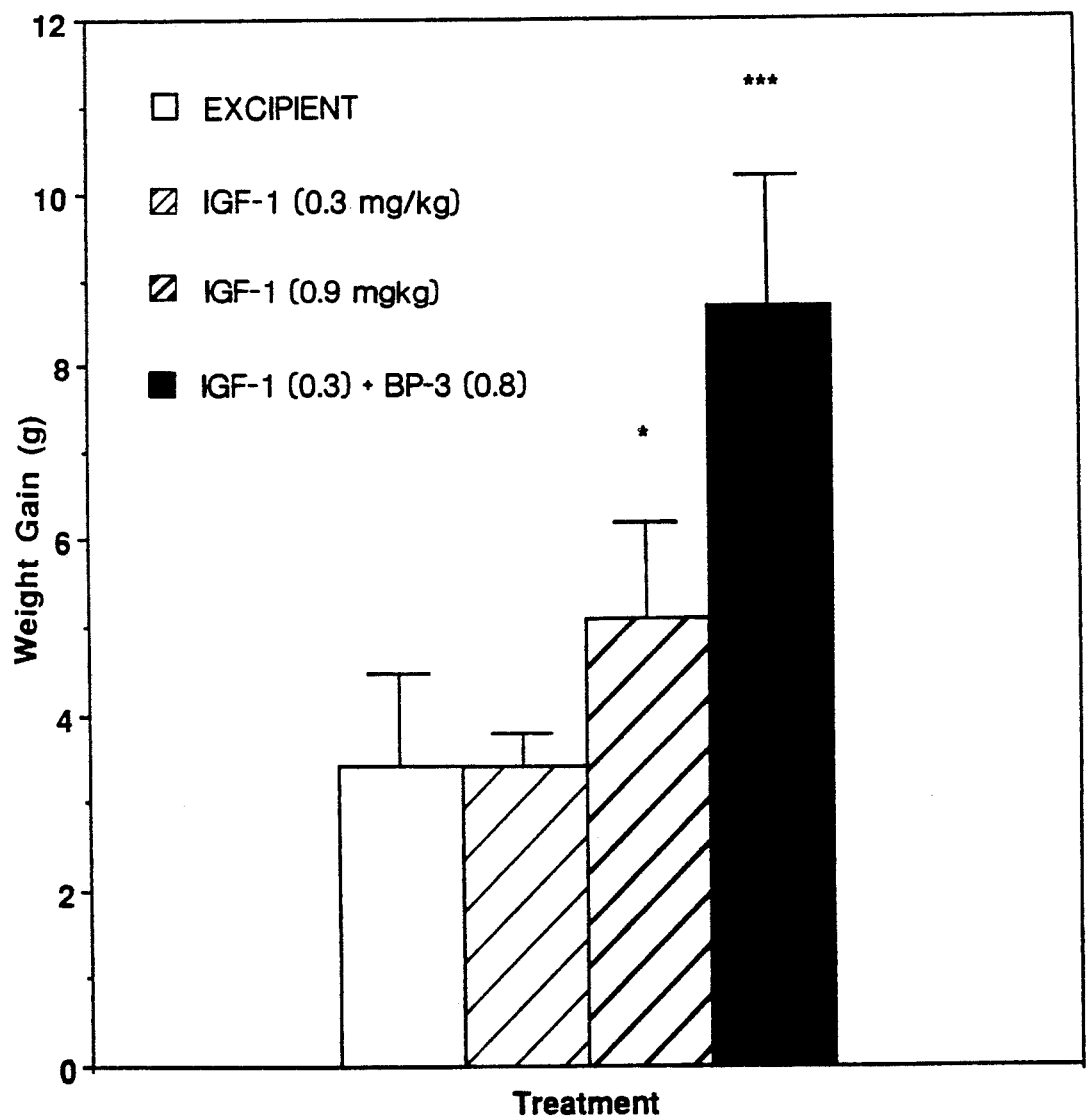
FIG. 6 illustrates the effect on weight gain of excipient, IGF-I (in two different doses), and IGF-I plus IGFBP-3 delivered to hypophysectomized rats as described for FIG. 5 after three-day treatment.

Excipient-treated hypophysectomized rats showed a small weight gain during the experiment. The low dose of IGF-I (0.3 mg/kg/day) did not increase weight gain, but the high dose (0.9 mg/kg/day) did produce a small weight gain. Surprisingly, when the low dose of IGF-I that produced no weight gain by itself was delivered coupled to IGFBP-3, there was a large amount of weight gain induced. FIG. 6 shows this data, where statistical comparisons were by ANOVA followed by Duncan's Test, with *** representing $p<0.001$ vs. excipient and high and low doses of IGF-I, and * representing $p<0.05$ vs. excipient.

Figure 7:
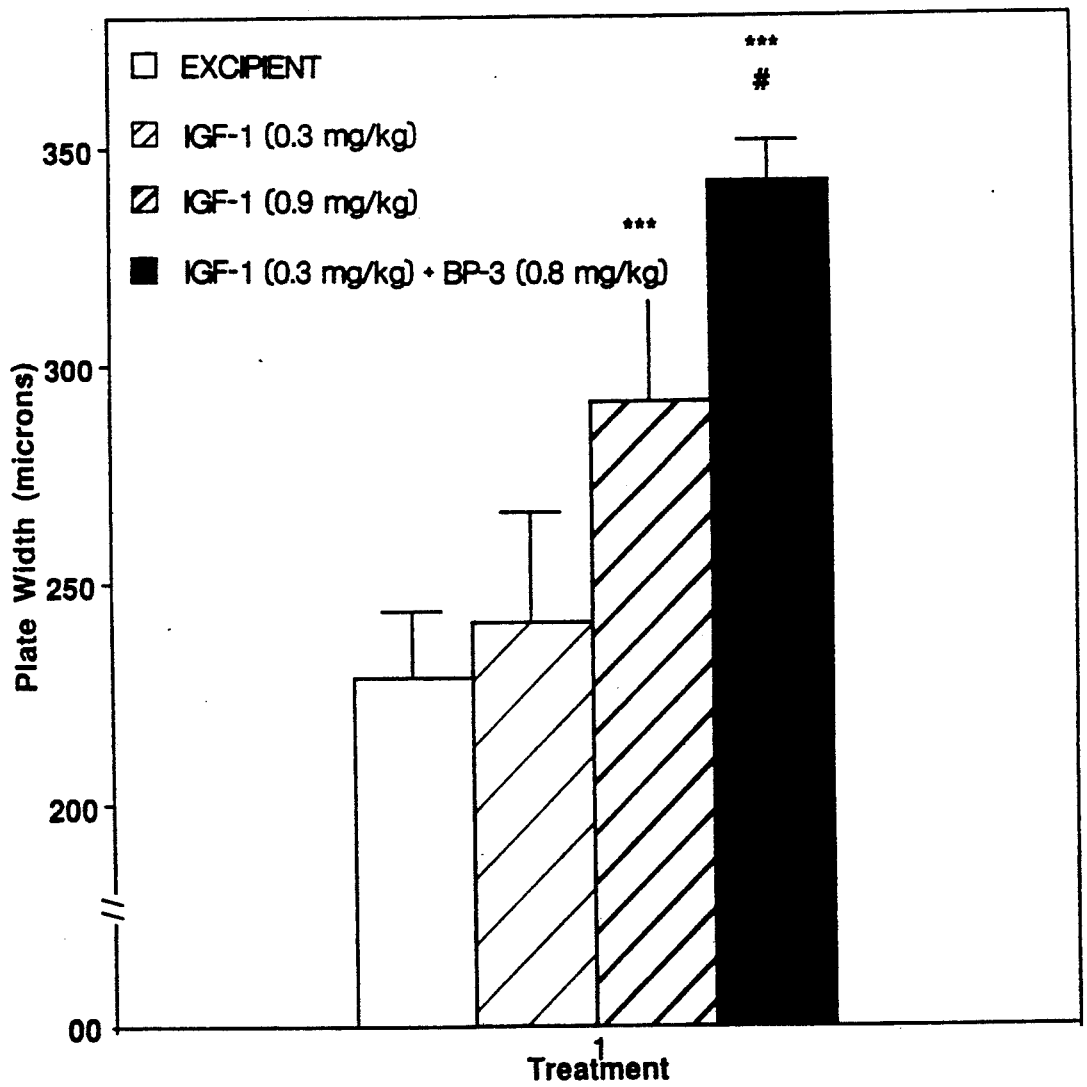
FIG. 7 illustrates the effect on tibial epiphyseal plate width of excipient, IGF-I (in two different doses), and IGF-I plus IGFBP-3 delivered to hypophysectomized rats as described for FIG. 6.

At sacrifice, a tibia was removed and the proximal region was fixed in formalin, decalcified, sectioned longitudinally, stained, and examined under a light microscope using a micrometer to measure the epiphyseal plate width. FIG. 7 shows the results. Statistical comparisons were by ANOVA followed by Duncan's Test, with the symbols in FIG. 7 indicating statistical significance compared to excipient-treated controls (*** $p<0.001$ or # $p<0.01$, versus high doses of IGF-I). The mean plate width in the excipient-treated hypophysectomized controls was 228 microns, in line with the historical data obtained. The low dose of IGF-I did not significantly increase plate width, while the high dose of IGF-I gave significant bone growth (mean 291 microns). Once again, the combination of IGF-I and IGFBP-3 resulted in a very large bone growth.

The organ weights, both absolute and relative, were unchanged for the liver, spleen, thymus, and heart. The absolute kidney weight was unchanged but the relative kidney weight was increased (comparing the IGF-I-plus IGFBP-3-treated rats with excipient and low-dose IGF-I groups ($p<0.05$)).

Conclusions from Examples I to III

Significant anabolic properties of IGF-I are observed only when free IGF-I is delivered by slow infusion. Multiple injections of IGF-I, for example, given twice a day, are relatively ineffective at inducing anabolic responses. Co-administration of IGF-I and IGFBP-3 as a sc infusion did not improve the efficacy of the IGF-I. It was only when IGF-I and IGFBP-3 were given as a bolus sc injection that an enhancement of the growth-promoting activity of IGF-I was observed. It is seen that IGFBP-3 inhibits the hypoglycemia induced by a large dose of IGF-I. Thus, IGF-I delivered by bolus sc injections coupled to IGFBP would allow less frequent injections to be given with a broader therapeutic index as short-term metabolic responses (hypoglycemia) would be minimized.

As IGF-I bound to a IGFBP has a prolonged half-life in vivo, this mode of delivering IGF-I will maintain circulating blood IGF-I. Thus, IGFBPs have the potential for a sustained-release system for delivering large amounts of IGF-I by sc injection. Further, because IGF-I circulating in the blood has anabolic activity, this means of delivering IGF-I should enhance the anabolic properties of IGF-I, thereby improving the ratio of the short-term metabolic effects to the long-term anabolic properties of IGF-I. A preferred form of IGF-I to administer is des-IGF-I, which will not bind to the other IGFBPs when it becomes disassociated from the IGFBP-3 and thus is expected to be more active than full-length IGF-I.

EXAMPLE IV

Two Clinical Scenarios for the Combination Treatment

Two examples of pertinent clinical scenarios are described below that will undoubtedly benefit from concomitant administration of an IGFBP, preferably IGFBP-3, and IGF-I:

1) Patients who exhibit a slowing in growth rate after at least twelve months of GH administration.

Figure 8A:
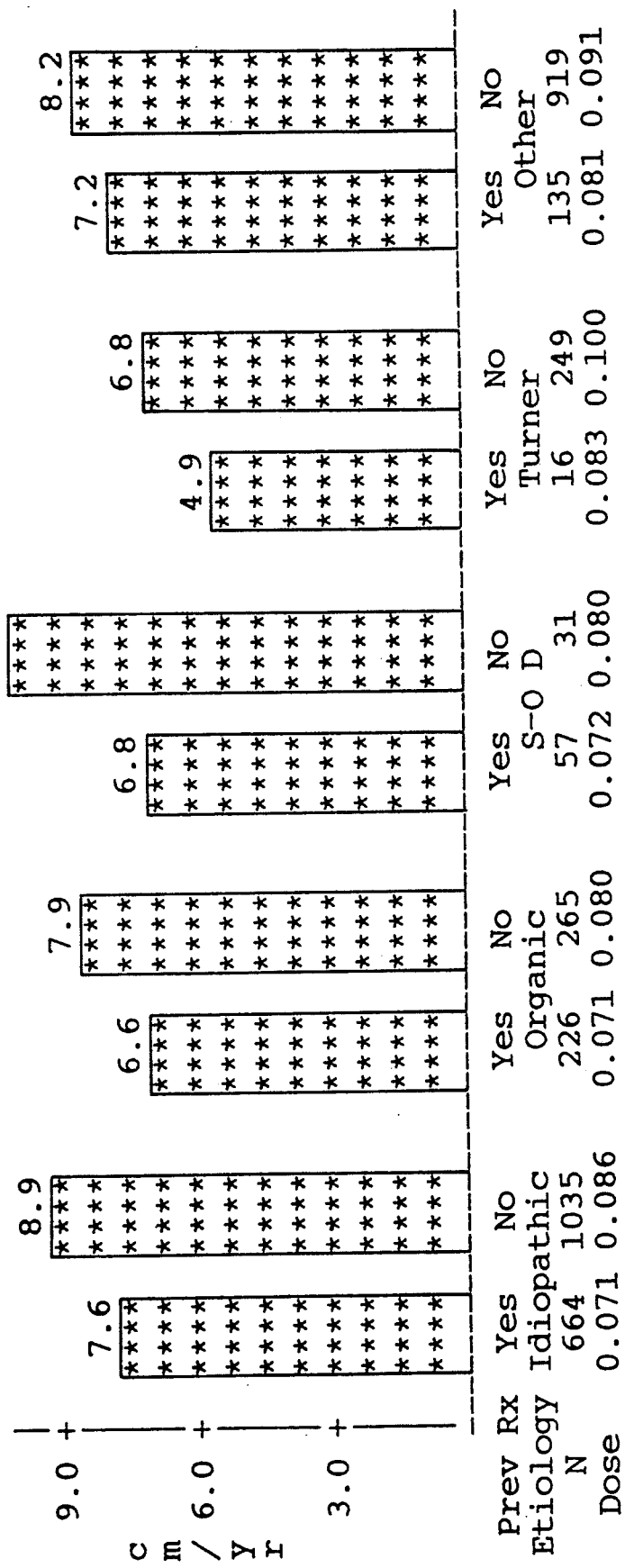
FIG. 8A is the data for the first year of hGH treatment and FIG. 8B is for the second year of hGH treatment.
Figure 8B:
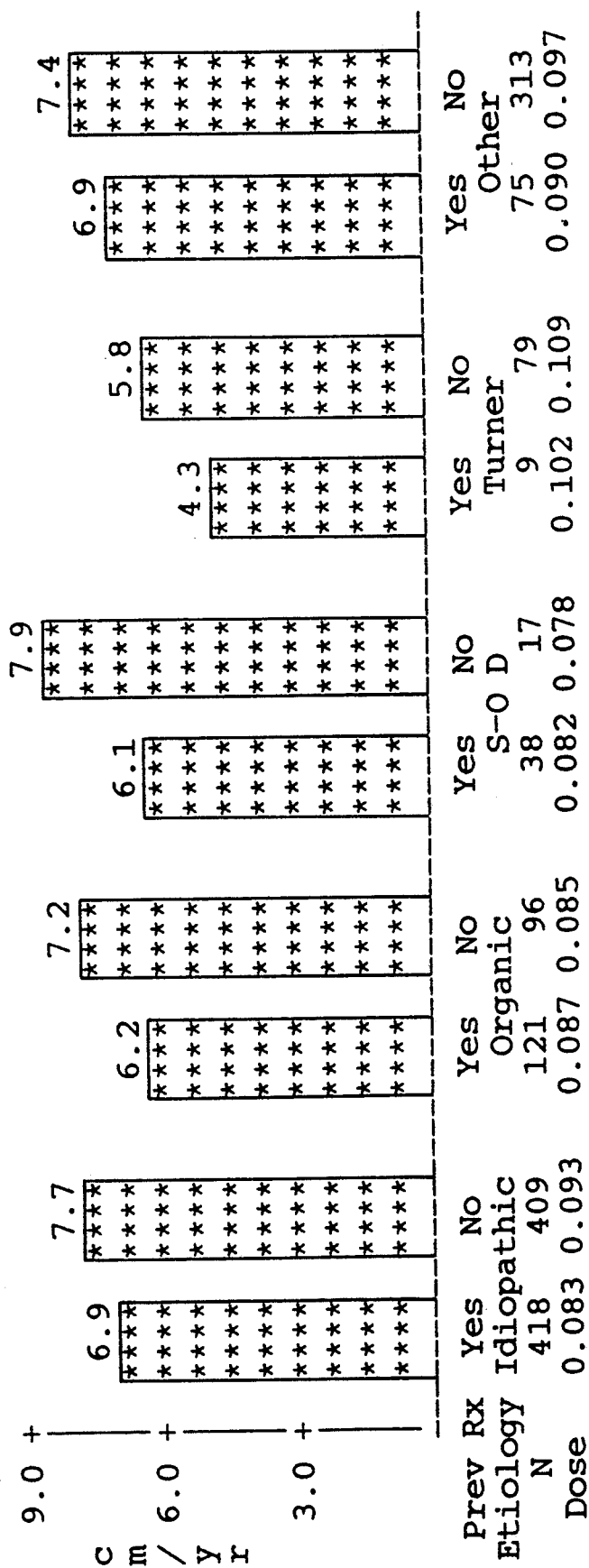

It is well recognized by pediatric endocrinologists that either naive (no previous treatment) or previously treated patients (following a break in GH administration) exhibit a second-year fall in growth rate. This phenomenon is independent of the etiology of the type of short stature or GH deficiency (e.g., whether idiopathic, organic, septo-optic dysplasia (S-O D), Turner, or other). See FIG. 8.

Thus, during the period where the growth rate is slowing, treatment with IGF-I together with a IGFBP would increase the annualized rate to compensate for this second-year loss in response.

2) Patients who have little time for GH administration to be maximally effective.

Figure 9:
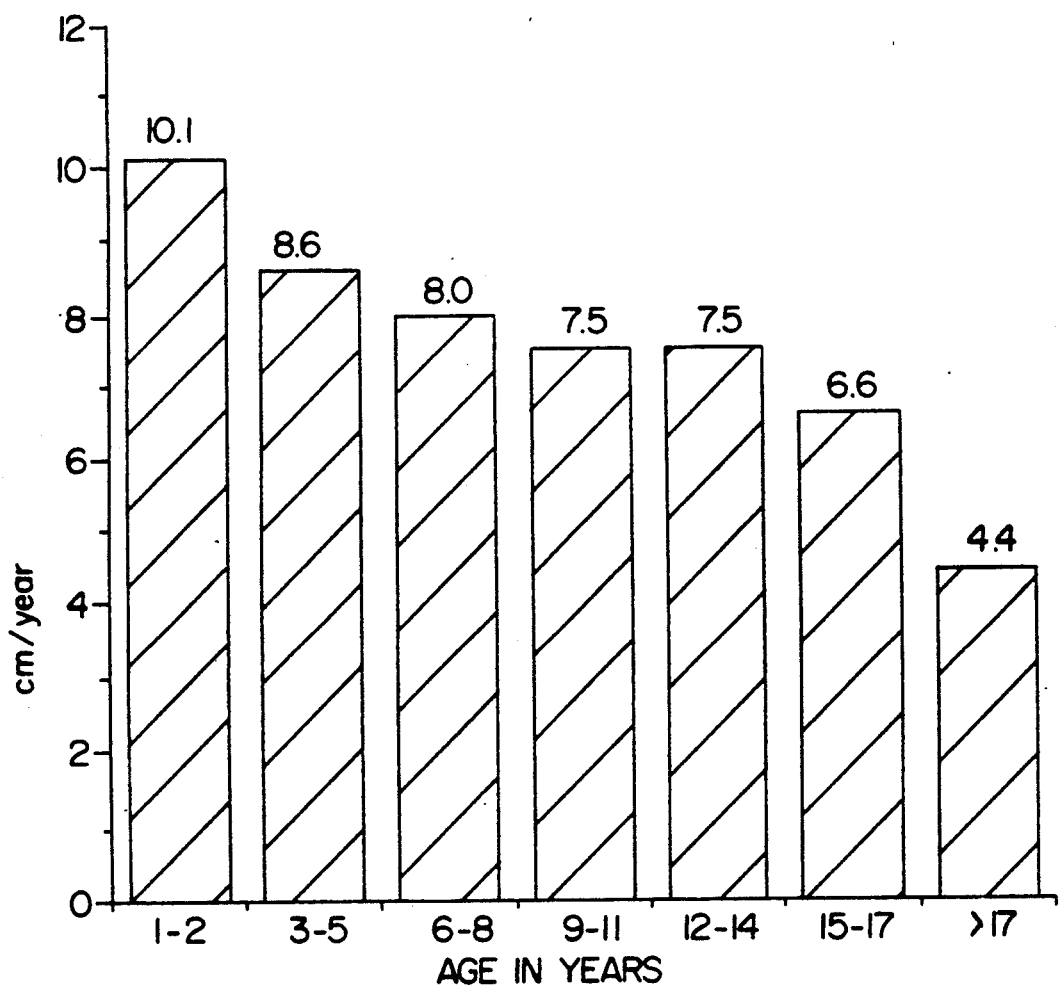
FIG. 9 illustrates bar graphs of the annualized (12-month) growth rate in cm/year of patients treated with the indicated dose of hGH in the 1-2, 3-5, 6-8, 9-11, 12-14, 15-17, and more than 17 year ranges. N indicates the number of patients in each age group.

If patients are older when they are diagnosed with GH deficiency, less time is available to correct their resultant short stature. This is illustrated in FIG. 9, where the annualized growth rate is reported for patients in seven age groups. Older patients have only, for example, 2-3 years left before their growth plates close, making further linear growth unlikely. These patients could be treated with the combination of IGF-I and an IGFBP to allow optimization of their growth rates.

DISCUSSION AND SUMMARY

The results shown herein have significance in medicine and agriculture in any situation where IGF-I treatment is used. This regime of combined IGF-I and IGFBP treatment would allow smaller doses of IGF-I (at least about nine-fold less) to be given to produce equivalent responses to treatment with IGF-I alone. This would be of particular importance in situations where the side effects of IGF-I treatment (i.e., hypoglycemia) should be minimized.

What is claimed is:

1. A method for producing an anabolic state in a mammal comprising co-administering to the mammal by subcutaneous bolus injection effective amounts of IGFBP-3 and IGF-I in a molar ratio of IGFBP-3 to IGF-I of about 0.5:1 to about 3:1 so as to produce a greater anabolic state in the mammal than that achieved using an equivalent dose of IGF-I alone, wherein growth hormone is not also administered to the mammal.

2. The method of claim 1 wherein the mammal is an animal.

3. The method of claim 2 wherein the IGF-I and IGFBP-3 are bovine, ovine, or porcine IGF-I and IGFBP-3, and the animal is bovine, ovine, or porcine, respectively.

4. The method of claim 1 wherein the mammal is a human.

5. The method of claim 4 wherein the IGF-I is human native-sequence, mature IGF-I and the IGFBP-3 is human IGFBP-3.

6. The method of claim 5 wherein the IGF-I is in a sterile, isotonic solution containing a citrate buffer, pH 6.

7. The method of claim 5 wherein the molar ratio of IGFBP-3 to IGF-I is about 0.8:1 to 1.5:1.

8. The method of claim 4 wherein the IGF-I is a human native-sequence IGF-I analog having the glutamic acid at position 3 replaced by another amino acid or deleted.

9. The method of claim 8 wherein the IGF-I is des(1-3)-IGF-I.

10. The method of claim 9 wherein the des(1-3)-IGF-I is in a sterile, isotonic solution containing acetic acid, pH 3.2 to 4.5.

11. The method of claim 8 wherein the IGFBP-3 is human IGFBP-3.

12. The method of claim 1 wherein the effective amount of IGF-I is at least 0.1 mg/kg/day.

13. The method of claim 4 wherein the effective amount of IGF-I is 1-20 mg/kg/day.

14. The method of claim 4 wherein the human to be treated has reached a maximum growth level and then a decrease in annualized growth rate after having previously been treated with growth hormone alone.

15. The method of claim 4 wherein the human to be treated is at an age that is 2-3 years before his or her growth plate closes.

16. The method of claim 4 wherein the effective amount of IGF-I is less than the dose that gives a maximal growth response using IGF-I alone.

17. The method of claim 4 wherein the human to be treated is a pregnant woman.

* * * * *